US00PP21435P2

(12) United States Plant Patent
Oates

(10) Patent No.: US PP21,435 P2
(45) Date of Patent: Nov. 2, 2010

(54) ***ECHEVERIA* PLANT NAMED 'JOEY2'**

(50) Latin Name: ***Echeveria setosa*×*E. gibbiflora***
Varietal Denomination: Joey2

(76) Inventor: John Oates, PO Box 3037, Tuross Head, NSW (AU) 2537

( * ) Notice: Subject to any disclaimer, the term of this patent is extended or adjusted under 35 U.S.C. 154(b) by 0 days.

(21) Appl. No.: 12/459,819

(22) Filed: Jul. 7, 2009

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—June Hwu

(57) ABSTRACT

A new and distinct *Echeveria* cultivar named 'Joey2' is disclosed, characterized a multiple, self-initiating branching habit, strong, uniform leaf color over a wide temperature range and under low water stress. Additionally, the new variety produces a high number of flower stems, with the peak amount in spring. The new variety is an *Echeveria*, typically produced as a garden or container plant.

1 Drawing Sheet

Figure 1:
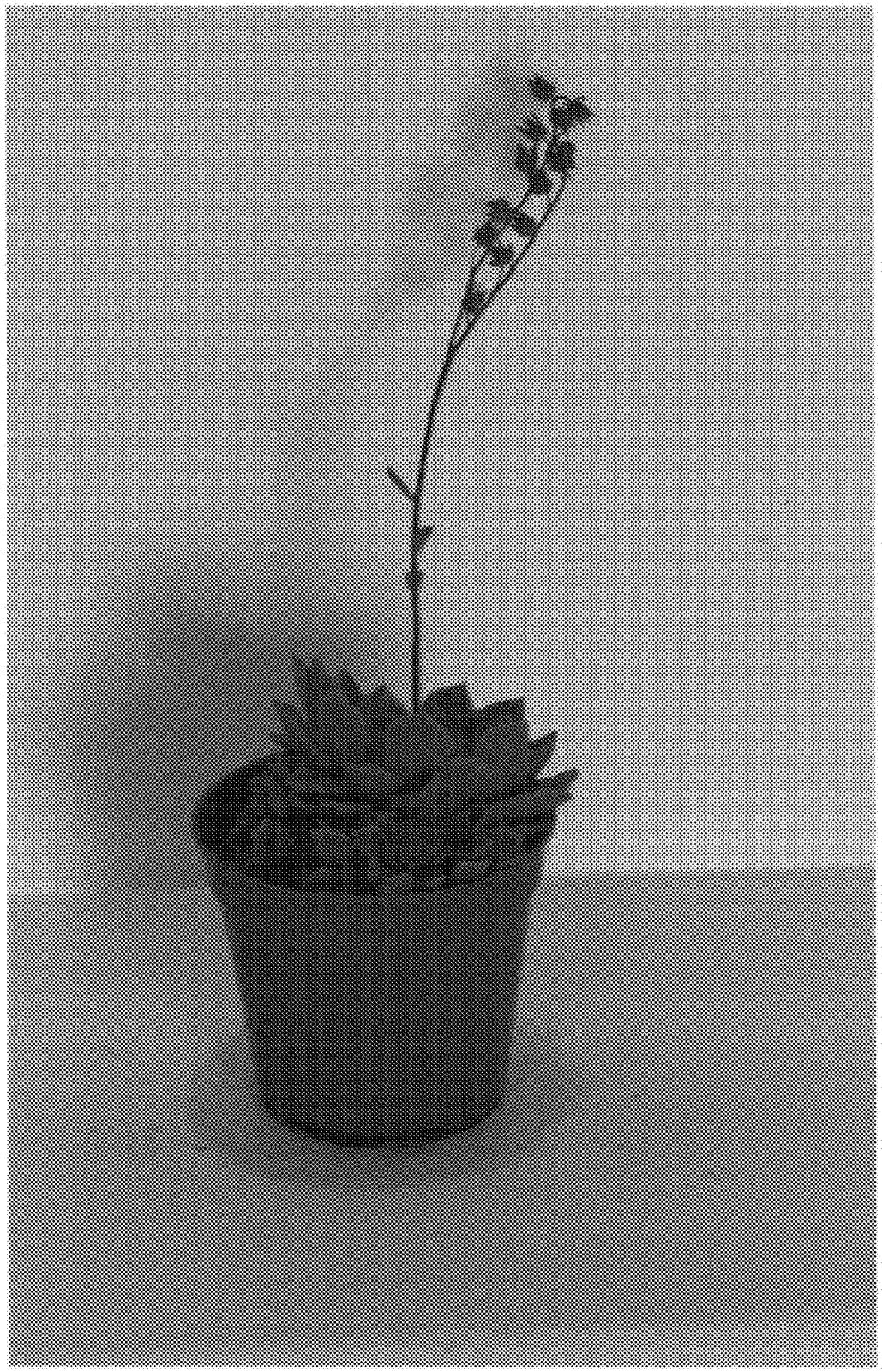

Latin name of the genus and species; *Echeveria setosa*×*E. gibbiflora.*

Variety denomination: 'Joey2'.

BACKGROUND OF THE INVENTION

The new cultivar is a product of a planned breeding program. The new variety originated from a cross pollination of the seed parent, an unpatented proprietary selection of *Echeveria setosa* referred to as '180' with the pollen parent, an unpatented proprietary selection of *Echeveria gibbiflora* referred to as '176' directed by the inventor in April of 2003. The crossing was made in Yowrie, New South Wales, Australia, at a commercial greenhouse.

'Joey2' was discovered by the inventor, John Oates, in June 2004 in Glenfield, New South Wales, Australia, at a commercial greenhouse among seedlings resulting from the 2003 crossing.

Asexual reproduction of the new cultivar 'Joey2' was first performed in Glenfield, New South Wales, Australia, at a commercial greenhouse by leaf cuttings in September 2004. 'Joey2' has since produced several generations and has shown that the unique features of this cultivar are stable and reproduced true to type.

SUMMARY OF THE INVENTION

The cultivar 'Joey2' has not been observed under all possible environmental conditions.

The phenotype may vary somewhat with variations in environment such as temperature, day length, and light intensity, without, however, any variance in genotype.

The following traits have been repeatedly observed and are determined to be the unique characteristics of 'Joey2'. These characteristics in combination distinguish 'Joey2' as a new and distinct *Echeveria* cultivar:

1. Self-initiating branching habit, producing profuse offshoots.
2. Maintains strong leaf color over wide temperature range and under low water stress.
3. High number of flower stems, maximizing in spring.

PARENTAL COMPARISON

Plants of the new cultivar 'Joey2' are similar to the female parent '180' in most horticultural characteristics. However, 'Joey2' differs in producing more offshoots, a more stable leaf color, more flowering stems and a glabrous instead of ciliate leaf margin.

Plants of the new cultivar 'Joey2' are similar to the male parent '182' in most horticultural characteristics. However, 'Joey2' differs in producing many more offshoots and having a different foliage color. Additionally, the new variety has a glabrous leaf surface, compared to the hirsute texture of '176', and a different leaf shape and margin. Also, the new variety produces more flowering stems than '176'.

COMMERCIAL COMPARISON

'Joey2' can be compared to the unpatented commercial variety *Echeveria* 'Green Ripple'. Plants of 'Green Ripple' are similar to plants of 'Joey2' in most horticultural characteristics, however, 'Joey2' produces more sideshoots, and more flowering stems. Additionally, 'Joey2' maintains the same foliage color under a variety of environmental conditions, whereas 'Emerald Ripple' has a foliage color that varies under different environmental conditions.

'Joey2' can also be compared to 'Joey1,' currently under review for U.S. plant patent, having Ser. No. 12/384,131. Plants of 'Joey2' are similar to plants of 'Joey1' in most horticultural characteristics, however, plants of 'Joey2' have a lighter foliage color and different leaf shape.

BRIEF DESCRIPTION OF THE PHOTOGRAPH

The accompanying photograph in FIG. 1 illustrates in full color a typical plant of 'Joey2' grown outdoors in Bonsall, Calif. This plant is approximately 1 year old, shown in a 4 inch pot. The inflorescence shows aged flowers, and the plant is beginning to produce the characteristic offsets. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'Joey2' plants grown outdoors in Bonsall, Calif. Temperatures ranged from 2° C. to 28° C. night and day. No artificial light, photoperiodic treatments or chemical treatments were given to the plants. Measurements and numerical values represent averages of typical plant types.

Botanical classification: *Echeveria setosa*×*E. gibbiflora* 'Joey2':

Age of the plant described: Approximately 1 year.

Container size of the plant described: 4 inch.

PROPAGATION

Time to initiate roots: About 12 to 20 days at approximately 20° C.

Time to produce a rooted young plant: Approximately 50 days.

Propagation method: Leaf cuttings.

Root description: Fibrous.

PLANT

Growth habit: Rosulate plant, sessile, non-branching, freely produces side off-shoots.

Height: Measured from soil level at top of pot, approximately 5 cm to top of highest leaf. Approximately 23 cm to top of highest inflorescence.

Plant spread: Approximately 12 cm.

Growth rate: Moderate.

Number of leaves per rosette: Approximately 45.

FOLIAGE

Leaf:

*Shape of blade.*—Spatulate.

*Apex.*—Apiculate.

*Base.*—Cuneate.

*Margin.*—Entire.

*Texture of top surface.*—Glabrous.

*Texture of bottom surface.*—Glabrous.

*Color.*—Young foliage upper side: Near RHS Green 143A. Base near Yellow-Green 144D. Young foliage under side: Near RHS Green 143B. Base near Yellow-Green 144D. Mature foliage upper side: Near RHS Green N138B. Base near Yellow-Green 144D. Mature foliage under side: Near RHS Green 143A. Base near Yellow-Green 144D.

Venation:

*Type.*—Parallel.

*Venation color.*—Indistinguishable.

Petiole: Not present, sessile.

FLOWER

Natural flowering season: Spring.

Inflorescence type and habit: Elongated peduncles arise from lateral portions of rosette. Terminates in 2 corymbs. Flowers approximately same size throughout corymb.

Rate of flower opening: More than 2 weeks to fully opened individual flower.

Flower longevity on plant: 6 to 7 weeks.

Quantity of flowers: 10 per corymb.

Total inflorescence size:

*Height.*—Approximately 9.0 cm.

*Width.*—Approximately 10.0 cm.

Quantity of inflorescences: 2 to 3 fully mature peduncles with 2 corymbs with open flowers at one time.

Individual flowers:

Corolla:

*Arrangement.*—Cylindrical shaped corolla, actinomorphic, flaring open at end. 5 separate petals, barely fused at base.

*Petal description.*—Quantity: 5. Length: Approximately 1.0 cm Width: Approximately 0.8 cm at widest point. Margin: Entire. Shape: Narrow deltoid. Apex: Acuminate. Base: Oblique. Texture: Matte.

*Color.*—Immature: Near RHS Orange-Red 31B. Fully opened interior: Near RHS Orange-Red 31A. Fully opened exterior: Near RHS Orange-Red 32B. Fading: Near RHS Orange-Red 31C, all surfaces.

Calyx:

*Arrangement.*—Actinomorphic, polysepalous.

*Sepal description.*—Quantity: 5. Length: Approximately 0.6 cm Width: Approximately 0.3 cm at widest point. Margin: Entire. Shape: Deltoid. Apex: Acute. Texture: Glabrous. Other characteristics: Fleshy. Color: Outer surface: Near RHS Yellow-Green 144B at base, upper 50% near RHS Red 42B. Inner surface: Near RHS Yellow-Green 144B at base, upper 50% near RHS Red 42B.

Bud:

*Shape.*—Acorn shape.

*Length.*—Approximately 0.8 cm.

*Diameter.*—Approximately 0.4 cm.

*Color.*—Near RHS Red 42C, base Near RHS Yellow-Green 144B.

Pedicels:

*Length.*—Approximately 0.6 cm.

*Width.*—Approximately 0.1 cm.

*Aspect.*—Straight, angled approximately 30° degrees from point of attachment.

*Color.*—Near RHS Yellow-Green 144A.

Peduncle:

*Length*—Approximately 12.5 cm.

*Width.*—Approximately 0.4 cm.

*Aspect.*—Straight. Approximately 75° angle from rosette.

*Strength.*—Very strong.

*Color.*—Near RHS Red 42D, lower 25% flushed with Yellow 2B.

Fragrance: None.

REPRODUCTIVE ORGANS

Stamens:

*Number.*—Average 10.

*Filament length.*—Approximately 0.4 cm.

*Filament color.*—Near RHS Yellow 9C.

*Anther length.*—Approximately 0.1 cm.

*Anther color.*—Near RHS Yellow 12A.

*Anther shape.*—Linear.

*Pollen.*—Not observed to date.

Pistil:

*Number.*—5.

*Length*(*including style*).—Approximately 0.7 cm.

*Style length.*—Approximately 0.2 cm.

*Style color.*—Near RHS Yellow-Green 150D.

*Stigma.*—Shape: Linear. Color: Near RHS Greyed-Orange 170B. Ovary color: Near RHS Green-Yellow 1D.

OTHER CHARACTERISTICS

Seeds and fruits: Not observed to date.

Disease/pest resistance: Neither tolerance nor resistance to normal diseases and pests of *Echeveria* have been observed.

Temperature tolerance: Tolerates temperatures from approximately 2° C. to at least 40° C.

Drought tolerance: Plant can survive for at least 2 weeks without supplemental water without a change in foliage color, or detrimental effects to the plant.

What is claimed is:

1. A new and distinct cultivar of *Echeveria* plant named 'Joey2' as herein illustrated and described.

* * * * *